United States Patent [19]
Gennery

[11] Patent Number: 5,910,502
[45] Date of Patent: Jun. 8, 1999

[54] USE OF LEVOBUPIVACAINE IN PAEDIATRIC SURGERY

[75] Inventor: Brian Albert Gennery, Cambridge, United Kingdom

[73] Assignee: Darwin Discovery Limited, United Kingdom

[21] Appl. No.: 09/034,070

[22] Filed: Mar. 3, 1998

[30] Foreign Application Priority Data

Mar. 3, 1997 [GB] United Kingdom .................... 9704351

[51] Int. Cl.⁶ ................................................. A61K 31/445
[52] U.S. Cl. .............................................................. 514/330
[58] Field of Search ............................................... 514/330

[56] References Cited

U.S. PATENT DOCUMENTS 5,708,011   1/1998   Bardsley et al. ........................ 514/330

OTHER PUBLICATIONS

Chem. Abs. #125:292849, Blanco et al. Reg. Anesth. 21(5), pp. 442–445, 1996.

*Primary Examiner*—Raymond Henley, III
*Attorney, Agent, or Firm*—Saliwanchik, Lloyd & Saliwanchik

[57] ABSTRACT

Levobupivacaine is used for providing anaesthesia or analgesia in human paediatric surgery.

6 Claims, No Drawings

USE OF LEVOBUPIVACAINE IN PAEDIATRIC SURGERY

FIELD OF THE INVENTION

This invention relates to a new therapeutic use for levobupivacaine or (S)-1-butyl-N-(2,6-dimethylphenyl)-2-piperidinecarboxamide.

BACKGROUND OF THE INVENTION

Racemic bupivacaine is an effective long-acting anaesthetic, and may be given as an epidural. However, racemic bupivacaine is cardiotoxic, having depressant electrophysiological and mechanical effects on the heart. It should therefore be used with caution in cardiac-compromised patients, and the use of high doses and high concentrations is contraindicated.

In particular, bupivacaine has produced death in a number of patients, including women in childbirth and when used in the Bier's block technique. Although the incidence of death has been relatively small, the concern has been sufficient to stop the use of 0.75% bupivacaine for obstetrics and the proscribing of bupivacaine for use in Bier's blocks.

In addition, due to its mode of action, directly on the nervous system, at higher doses, bupivacaine is known to have undesirable central nervous system (CNS) side-effects which, prima facie, are connected to its anaesthetic activity. Indeed, the occurrence of CNS side-effects is one of the major factors limiting the use of this drug in normal clinical practice employing techniques such as local infiltration, nerve block, field block, epidural and spinal blocks.

It has been suggested that levobupivacaine is less cardiotoxic than dextrobupivacaine and racemic bupivacaine. See, for example, Vanhoutte et al, Br. J. Pharmacol. 103: 1275–1281 (1991), and Denson et al, Regional Anaesthesia, 17: 311–316 (1992). However, these reports are based on work in vitro, and cannot necessarily be extrapolated to any mammals, and certainly not to humans.

The surprising and effective utility of levobupivacaine in man, in vivo, is evidenced for the first time in WO-A-9510276, WO-A-9510277 and Gristwood et al, Exp. Opin. Invest. Drugs 3 (11): 1209–12 (1994).

No long-acting anaesthetic is approved for use in paediatrics. Children are particularly concerned about surgery, making the control of anaesthesia a particular problem. A relatively narrow therapeutic window is available. Further, there is a potential problem with intubation, because of the small airway and associated risk of damage. Children have relatively undeveloped livers, therefore increasing the risk that there will be drug interaction. All these problems mean that long-acting general anaesthetics are not registered for use in paediatrics.

Because a child is in development, and has growing/dividing cells, a particular concern in using any drugs on a child is their long-term effect. It is therefore desirable to avoid the use of drugs that may have genotoxic properties, especially if the drugs are to be used often and over a prolonged period.

SUMMARY OF THE INVENTION

While it has previously been shown that the use of levobupivacaine may have advantages over bupivacaine in certain areas, there has been no evidence to suggest that it would be of value, in paediatrics. This invention is based on the surprising discovery that levobupivacaine is an effective and especially safe anaesthetic, for this purpose.

DESCRIPTION OF THE INVENTION

In the method of the present invention, levobupivacaine may be provided in solution, for infusion or injection into the epidural or spinal space, or for administration by any of the conventional means for obtaining a nerve or field block. In addition to the anaesthetic blocks conventionally provided by the racemate, levopbupivacaine may also be useful in providing blocks in areas of the body where the risk of systemic exposure to the drug, and therefore CNS side-effects, is particularly high. Examples include open wounds and vascular areas, for instance using intercostal blocks for the latter.

For upper limb surgery at least, infusion into the body near the base of the limb may be appropriate. A regional or plexus block may also be used.

Upper and lower extremity blocks may be used. Auxiliary, interscalene, sciatic, lumbar or plexus administration may be involved.

The invention is also suitable for use in neonates, e.g. up to 6 months or more, e.g. 2 years. For example, it may be used in caudal block, urological surgery or orchidopexy. In this context, low genotoxicity is particularly important.

Epidural infusion (intravascular administration) is especially suitable, when the plasma threshold is low. For example, it is suitable in treating subjects 0.5 to 12 years old. Levobupivacaine may be used in combination with fentanyl; see the other Application filed on the same day naming the same inventor and entitled "The Use of Levobupivacaine in Combination with Other Drugs".

Administration of levobupivacaine may be continuous or bolus administration. This may be done using conventional apparatus, e.g. including means for the patient to induce infusion as desired. The daily dose administered to the patient may be in the relatively low range known for the administration of racemic bupivacaine, but, because of the decreased CNS side-effects of levobupivacaine, may be higher than the conventional dose for the racemic drug. The total dose of levobupivacaine may be around, or in excess of, 2 mg per kg of patient body weight.

The concentration of levobupivacaine to be given can be that conventionally used for the racemic drug, e.g. from 0.25% w/v. However, the concentration may be higher than this, for instance, at least 0.75% w/v, and can be up to 2% w/v. Preferably, however, the concentration of levobupivacaine is about 0.5% w/v. The solution is preferably aqueous.

The solution may typically be put up in unit doses of from 1 to 15 ml, and preferably of around 10 ml. However, the unit doses may be higher, for instance up to 40 ml or higher. The unit doses may be in the form of ampoules, which may be made of any suitable material, e.g. glass or an appropriately impervious plastic material. Unit dosages comprising at least 75 mg, but preferably less than 200 mg, of levobupivacaine can be administered, and more preferably the unit dosage is in the range 80 to 150 mg. Additionally, low dose infusions may be appropriate, over a few hours up to a few days.

The administration of levobupivacaine over a range of concentrations, including those currently used for the racemic drug and the higher concentrations described above, can be carried out for significantly longer periods than at present, again as a result of the reduced CNS side-effects experienced with levobupivacaine. For instance, levobupivacaine can be administered to a patient safely for at least 24 hours, often up to 72 hours, and even for periods of up to a week or a fortnight, or longer. It can, of course, be administered for similar periods already used for the racemic drug, e.g. between 2 and 6 hours. Levobupivacaine may be particularly valuable for the maintenance of post-operative analgesia, e.g. over the period 8–24 hours after surgery.

The method of the present invention is particularly useful in surgical procedures carried out on patients who merely require surgery, and are otherwise healthy. The patient may also be cardiac or CNS-compromised, or predisposed to cardiac or CNS-related conditions, i.e. having a low CNS threshold.

For the purposes of this specification, the levobupivacaine is substantially free of dextrobupivacaine, i.e. in at least 90%, and most preferably at least 99%, enantiomeric excess with respect to dextrobupivacaine. Throughout this specification, reference to bupivacaine and its enantiomers includes pharmaceutically-acceptable salts thereof.

It has been found that, in the mouse lymphoma, bupivacaine dosage was limited by cytotoxicity and was positive for genotoxicity, while levobupivacaine was completely negative. This surprising result indicates the value of levobupivacaine in paediatric use, whether for neonates, e.g. up to 12 months old, or older children, e.g. up to 12 years old. It is also indicative of utility for lactating mothers, and more generally for women of child-bearing age, especially those not using contraceptive devices or drugs.

More specifically, levobupivacaine HCl was assayed for its ability to induce mutation at the tk locus (5-trifluorothymidine resistance) in mouse lymphoma cells using a fluctuation protocol. The study consisted of a cytotoxicity range-finder followed by two independent experiments, each conducted in the absence and presence of metabolic activation by an Aroclor 1254-induced rat liver post-mitochondrial fraction (S-9). For reference, bupivacaine HCl was tested concurrently in the cytotoxicity range-finder.

A wide range of concentrations were selected for the cytotoxicity range-finder experiments, separated by two-fold intervals and ranging from 31.25 to 1000 μg/ml for levobupivacaine HCl and from 62.5 to 2000 μg/ml for bupivacaine HCl (limited by solubility in both cases). Cells survived all doses of levobupivacaine HCl yielding 149.6% relative survival in the absence of S-9 and 9.1% relative survival in the presence of S-9 at the top dose (1000 μg/ml). The top two doses of bupivacaine HCl (1000 and 2000 μg/ml) were completely toxic but cells survived 500 μg/ml in the absence and presence of S-9, yielding 100% and 12.4% relative survival, respectively.

Accordingly, six doses of levobupivacaine HCl were chosen for the first experiment, separated by two-fold intervals and ranging from 31.25 to 1000 μg/ml. For reference, three doses of bupivacaine HCl were tested in the absence of S-9 (250, 500 and 750 μg/ml), and two doses in the presence of S-9 (250, 500 μg/ml). The lowest five doses of levobupivacaine HCl and all reference doses of bupivacaine HCl were selected to determined viability and 5-trifluorothymidine resistance, 2 days after treatment. The top dose of levobupivacaine HCl selected (500 μg/ml) yielded 80.9% and 41.3% relative survival in the absence and presence of S-9. The top dose of bupivacaine HCl in the presence of S-9 was excluded from analysis due to heterogeneity between the replicate cultures, attributable to high toxicity evident during the expression period. Thus, the top doses analysed were 750 and 250 μg/ml in the absence and presence of S-9, which yielded 75.4% relative and 54.3% relative survival, respectively.

In the second experiment, the dose range was modified slightly for both levobupivacaine HCl and bupivacaine HCl. For levobupivacaine HCl, the top doses analysed were 500 μg/ml and 1000 μg/ml in the absence and presence of S-9, which yielded 85.8% and 44.6% relative survival, respectively. The top doses of bupivacaine HCl anaylsed in this experiment were 750 and 500 μg/ml in the absence and presence of S-9, which yielded 46.0% and 50.8% relative survival, respectively.

Negative (solvent) and positive control treatments were included in each mutation experiment in the absence and presence of S-9. Mutant frequencies in negative control cultures fell within normal ranges, and clear increases in mutation were induced by the positive control chemicals 4-nitroquinoline 1-oxide (without S-9) and benzo[a]pyrene (with S-9). Therefore, the study was accepted as valid.

No statistically significant increases in mutant frequency were observed following treatment with levobupivacaine HCl at any dose level, in these experiments, in the absence or presence of S-9. For bupivacaine HCl, a statistically significant increase in mutant frequency was observed at 750 μg/ml in the second experiment, in the absence of S-9. However, significant heterogeneity in survival was observed between the replicate cultures at this dose, and the finding was not seen in the first experiment. No statistically significant increases in mutant frequency were observed following treatment with bupivacaine HCl in the presence of S-9 (again only a limited number of doses were tested for reference).

It is concluded that, under the conditions employed in this study, levobupivacaine HCl is not mutagenic in this test system.

In a clinical study, the suitability of levobupivacaine in paediatric surgery was evaluated. This was a double-blind randomized, placebo-controlled study, to determine the safety and effectiveness of levobupivacaine for field block in children having outpatient herniorrhaphy. More specifically, otherwise healthy children ages 6 mo to 12 y presenting for outpatient herniorrhaphy were randomized to receive either ilioinguinal/iliohytpogastric (IlIH) nerve block(s) with 0.25 ml/kg 0.5% levobupivacaine per side operated, or no block, at the completion of surgery. It was concluded that levobupivacaine was safe and effective for IlIH block in children having herniorrhaphy, as demonstrated by a longer interval to rescue analgesia, fewer rescue analgesic doses, lower CHEOPS at 15, 20, 30 and 60 min and the absence of any adverse events specifically attributable to levobupivacaine.

In a further study, using levobupivacaine in patients requiring hernia repair, 45% of patients in the 0.5% levobupivacaine group compared with 73.3% of patients in the no block required at least one dose of rescue analgesia (p=0.167). The majority of the children who required rescue (91.4%) required two or fewer doses of rescue analgesia. The time to first request for rescue medication was significantly longer in the 0.5% levobupivacaine group compared with the no block group. The median patient in the 0.5% levobupivacaine group first requested rescue medication after at least 118 minutes, compared with 31 minutes in the no block group (p=0.041).

I claim:

1. A method of providing anaesthesia or analgesia in human paediatric surgery, which comprises the administration of levobupivacaine.

2. The method, according to claim 1, wherein said human is a neonate.

3. The method, according to claim 1, wherein said human is 0.5 to 12 years old.

4. The method, according to claim 1, wherein said administration is by epidural infusion.

5. The method, according to claim 1, wherein said administration comprises an upper or lower extremity block.

6. The method, according to claim 1, for use in post-operative pain control.

* * * * *

UNITED STATES PATENT AND TRADEMARK OFFICE
CERTIFICATE OF CORRECTION

PATENT NO. : 5,910,502

DATED : June 8, 1999

INVENTOR(S) : Brian Albert Gennery

It is certified that error appears in the above-identified patent and that said Letters Patent is hereby corrected as shown below:

*In the Claims*

Column 4, line 61:

"A method of providing anaesthesia or analgesia in human paediatric surgery, which comprises the administration of levobupivacaine."

should read:

--A method of providing anaesthesia or analgesia in human paediatric surgery, which comprises the administration of levobupivacaine, wherein said levobupivacaine is present in an enantiomeric excess of at least about 90% with respect to dexbupivacaine.--

Signed and Sealed this

Thirtieth Day of November, 1999

Attest:

Q. TODD DICKINSON

*Attesting Officer*     *Acting Commissioner of Patents and Trademarks*